US007985209B2

(12) United States Patent
Villanueva et al.

(10) Patent No.: US 7,985,209 B2
(45) Date of Patent: Jul. 26, 2011

(54) WOUND OR SURGICAL DRESSING

(75) Inventors: Julie M. Villanueva, Decatur, GA (US);
Curtis Neil Sayre, Atlanta, GA (US);
Lei Huang, Duluth, GA (US); Kevin Peter McGrath, Alpharetta, GA (US);
Ning Wei, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 719 days.

(21) Appl. No.: 11/303,011

(22) Filed: Dec. 15, 2005

(65) Prior Publication Data
US 2007/0141130 A1    Jun. 21, 2007

(51) Int. Cl.
*A61F 13/02* (2006.01)
(52) U.S. Cl. ......... 604/307; 424/682; 424/685; 514/191
(58) Field of Classification Search ................... 604/307; 514/191; 424/682, 685
See application file for complete search history.

(56) References Cited

U.S. PATENT DOCUMENTS

| | | | |
|---|---|---|---|
| 3,338,992 A * | 8/1967 | Kinney | |
| 3,341,394 A * | 9/1967 | Kinney | |
| 3,494,821 A | 2/1970 | Evans | |
| 3,502,538 A * | 3/1970 | Peterson | |
| 3,502,763 A * | 3/1970 | Hartmann | |
| 3,542,615 A * | 11/1970 | Dobo et al. | |
| 3,692,618 A * | 9/1972 | Dorschner et al. | |
| 3,802,817 A * | 4/1974 | Matsuki et al. | |
| 3,849,241 A * | 11/1974 | Butin et al. | |
| 4,041,203 A * | 8/1977 | Brock et al. | |
| 4,076,673 A | 2/1978 | Burkholder, Jr. | |
| 4,100,324 A * | 7/1978 | Anderson et al. | |
| 4,144,370 A | 3/1979 | Boulton | |
| 4,215,682 A * | 8/1980 | Kubik et al. | |
| 4,285,343 A | 8/1981 | McNair | |
| 4,340,563 A * | 7/1982 | Appel et al. | |
| 4,375,448 A * | 3/1983 | Appel et al. | |
| 4,375,718 A * | 3/1983 | Wadsworth et al. | |
| 4,494,278 A * | 1/1985 | Kroyer et al. | |
| 4,592,815 A * | 6/1986 | Nakao | |
| 4,608,047 A | 8/1986 | Mattingly | |
| 4,666,647 A | 5/1987 | Enloe et al. | |
| 4,687,478 A | 8/1987 | Van Tilburg | |
| 4,704,116 A | 11/1987 | Enloe | |
| 4,708,870 A * | 11/1987 | Pardini | |
| 4,741,941 A * | 5/1988 | Englebert et al. | |
| 4,766,029 A * | 8/1988 | Brock et al. | |
| 4,775,582 A * | 10/1988 | Abba et al. | |
| 4,798,603 A | 1/1989 | Meyer et al. | |
| 4,818,464 A * | 4/1989 | Lau | |
| 4,818,598 A * | 4/1989 | Wong | |
| 4,833,003 A * | 5/1989 | Win et al. | |
| 4,853,281 A * | 8/1989 | Win et al. | |
| 4,874,659 A * | 10/1989 | Ando et al. | |
| 4,886,512 A | 12/1989 | Damico et al. | |
| 4,921,701 A * | 5/1990 | Blehm Blank | |
| 4,927,582 A | 5/1990 | Bryson | |
| 4,950,264 A | 8/1990 | Osborn, III | |
| 5,009,653 A | 4/1991 | Osborn, III | |
| 5,057,361 A | 10/1991 | Sayovitz et al. | |
| 5,085,654 A | 2/1992 | Buell | |
| 5,143,679 A * | 9/1992 | Weber et al. | |
| 5,151,092 A * | 9/1992 | Buell et al. | |
| 5,167,897 A * | 12/1992 | Weber et al. | |
| 5,169,706 A * | 12/1992 | Collier et al. | |
| 5,176,668 A | 1/1993 | Bernardin | |
| 5,176,672 A | 1/1993 | Bruemmer et al. | |
| 5,190,563 A | 3/1993 | Herron et al. | |
| 5,192,606 A | 3/1993 | Proxmire et al. | |
| 5,196,000 A * | 3/1993 | Clear et al. | |
| 5,197,959 A | 3/1993 | Buell | |
| 5,217,576 A | 6/1993 | Van Phan | |
| 5,267,992 A | 12/1993 | Van Tilburg | |
| 5,284,703 A | 2/1994 | Everhart et al. | |
| 5,308,346 A | 5/1994 | Sneller et al. | |
| 5,342,342 A | 8/1994 | Kitaoka | |
| 5,350,624 A | 9/1994 | Georger et al. | |
| 5,382,400 A * | 1/1995 | Pike et al. | |
| 5,401,446 A * | 3/1995 | Tsai et al. | |

(Continued)

FOREIGN PATENT DOCUMENTS

AU            510720         7/1980
(Continued)

OTHER PUBLICATIONS

Batich et al., Absorbent Materials with Covalently-Bonded, Nonleachable, Polymeric antimicrobial Surfaces, and Methods for Preperation, May 15, 2003, International Applicantion Published Under the PCT, WO 03/039602 A2.*
Krema, R., et al. "What's New in Highloft Production?" *Nonwovens Industry*, pp. 74-78, Oct. 1997.
Fairhust, D., et al "Zeta Potential Measurements of Irregular Shape Solid Materials" *Particle Size Distribution II, Assessment and Characterization* ACS Symposium Series 472, ISBN 0-8412-2117-0, pp. 337-353, 1991.
Derwent Abstract, CN 1057807C, Shu J., Oct. 2000.
Derwent Abstract, JP 4119169A, Kanebo Ltd, Apr. 1992.
Derwent Abstract, JP 4197409A, Unitika Res Lab KK, Jul. 1992.
Derwent Abstract, JP 5226187A, Toray Ind Inc, Sep. 1993.

(Continued)

*Primary Examiner* — Sabiha Qazi
*Assistant Examiner* — Ali Soroush
(74) *Attorney, Agent, or Firm* — Dority & Manning, P.A.

(57) ABSTRACT

A wound or surgical dressing is disclosed. The wound or surgical dressing is configured to cover or surround a wound, a surgical incision, or any type of skin irritation. In accordance with the present disclosure, the wound or surgical dressing is treated with a bacteriostatic composition that is capable of binding and trapping negatively charged matter, such as bacteria, pathogens, and the like. The bacteriostatic composition comprises a cationic polymer, a cationic oligomer, or particles coated with a cationic material. The bacteriostatic composition is bonded to the wound or surgical dressing in a manner such that the bacteriostatic composition is not substantially transferred to a patient being treated.

29 Claims, 2 Drawing Sheets

U.S. PATENT DOCUMENTS

| | | | |
|---|---|---|---|
| 5,407,600 A | | 4/1995 | Ando et al. |
| 5,464,688 A * | | 11/1995 | Timmons et al. |
| 5,486,166 A | | 1/1996 | Bishop et al. |
| 5,490,846 A | | 2/1996 | Ellis et al. |
| 5,509,914 A | | 4/1996 | Osborn, III |
| 5,509,915 A | | 4/1996 | Hanson et al. |
| 5,527,171 A * | | 6/1996 | Soerensen |
| 5,540,332 A | | 7/1996 | Kopacz et al. |
| 5,558,659 A | | 9/1996 | Sherrod et al. |
| 5,569,234 A | | 10/1996 | Buell et al. |
| 5,634,916 A | | 6/1997 | Lavon et al. |
| 5,649,916 A | | 7/1997 | DiPalma et al. |
| 5,667,635 A | | 9/1997 | Win et al. |
| 5,702,378 A | | 12/1997 | Widlund et al. |
| 5,709,798 A | | 1/1998 | Adiletta |
| 5,716,349 A | | 2/1998 | Taylor et al. |
| 5,756,111 A | | 5/1998 | Yoshikawa et al. |
| 5,785,179 A | | 7/1998 | Buczwinski et al. |
| 5,853,883 A * | | 12/1998 | Nohr et al. |
| 5,858,515 A * | | 1/1999 | Stokes et al. |
| 5,888,524 A | | 3/1999 | Cole |
| 5,964,351 A | | 10/1999 | Zander |
| 5,964,742 A * | | 10/1999 | McCormack et al. |
| 5,968,488 A | | 10/1999 | Wachter et al. |
| 5,976,117 A * | | 11/1999 | Dunshee et al. ............. 604/307 |
| 6,001,303 A * | | 12/1999 | Haynes et al. |
| 6,028,018 A | | 2/2000 | Amundson et al. |
| 6,030,331 A | | 2/2000 | Zander |
| 6,110,158 A | | 8/2000 | Kielpikowski |
| 6,150,002 A * | | 11/2000 | Varona |
| 6,158,614 A | | 12/2000 | Haines et al. |
| 6,197,404 B1 * | | 3/2001 | Varona |
| 6,231,719 B1 | | 5/2001 | Garvey et al. |
| 6,269,969 B1 | | 8/2001 | Huang et al. |
| 6,269,970 B1 | | 8/2001 | Huang et al. |
| 6,273,359 B1 | | 8/2001 | Newman et al. |
| 6,315,864 B2 | | 11/2001 | Anderson et al. |
| 6,330,735 B1 | | 12/2001 | Hahn et al. |
| 6,417,120 B1 * | | 7/2002 | Mitchler et al. |
| 6,440,437 B1 | | 8/2002 | Krzysik et al. |
| 6,511,465 B1 | | 1/2003 | Freiburger et al. |
| 6,531,531 B1 | | 3/2003 | Han |
| 6,607,994 B2 | | 8/2003 | Soane et al. |
| 6,613,729 B1 | | 9/2003 | Cole et al. |
| 6,617,362 B1 * | | 9/2003 | Ryu et al. |
| 6,630,096 B2 | | 10/2003 | Venturino et al. |
| 6,635,755 B1 | | 10/2003 | Jaschinski et al. |
| 6,663,611 B2 | | 12/2003 | Blaney et al. |
| 6,673,447 B2 | | 1/2004 | Wei et al. |
| 6,888,044 B2 | | 5/2005 | Fell et al. |
| 6,897,168 B2 * | | 5/2005 | Branham et al. ................ 442/59 |
| 7,141,518 B2 * | | 11/2006 | MacDonald et al. |
| 2002/0177828 A1 | | 11/2002 | Olderman et al. |
| 2003/0120253 A1 | | 6/2003 | Wentzel et al. |
| 2003/0203009 A1 | | 10/2003 | MacDonald |
| 2004/0009141 A1 | | 1/2004 | Koenig et al. |
| 2004/0060112 A1 | 4/2004 | Fell et al. |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084474 A1 | 4/2005 | Wu et al. |
| 2005/0085144 A1 | 4/2005 | MacDonald et al. |
| 2005/0137540 A1 * | 6/2005 | Villanueva et al. ........... 604/360 |
| 2006/0008442 A1 | 1/2006 | MacDonald et al. |
| 2006/0114754 A1 | 6/2006 | MacDonald et al. |
| 2007/0066482 A1 | 3/2007 | Thijssen et al. |
| 2007/0134337 A1 | 6/2007 | Villanueva et al. |
| 2007/0141934 A1 | 6/2007 | Sayre et al. |
| 2007/0142262 A1 | 6/2007 | Sayre et al. |
| 2008/0147029 A1 | 6/2008 | Pate et al. |

FOREIGN PATENT DOCUMENTS

| | | |
|---|---|---|
| CA | 19851180622 | 1/1985 |
| DE | 20011013557 A1 | 7/2001 |
| EP | 0794223 | 9/1997 |
| EP | 1291460 | 3/2003 |
| WO | WO 9826808 | 6/1998 |
| WO | WO 0036207 | 6/2000 |
| WO | WO 0036207 A1 | 6/2000 |
| WO | WO 0124840 | 4/2001 |
| WO | WO 0134656 | 5/2001 |
| WO | WO 0183665 | 11/2001 |
| WO | WO 0192632 | 12/2001 |
| WO | WO 03006739 | 1/2003 |
| WO | WO 03039602 A2 | 5/2003 |
| WO | WO 2004004679 | 1/2004 |
| WO | WO 2004038089 | 5/2004 |
| WO | WO 2004062703 | 7/2004 |
| WO | WO 2004110193 | 12/2004 |
| WO | WO 2005032252 | 4/2005 |
| WO | WO 2006111991 A1 | 10/2006 |

OTHER PUBLICATIONS

Cost, Frank "Pocket Guide to Digital Printing," Delmar Publishers, Albany New York, 1977: pp. 144-145.

"Colour and Constitution of Organic Molecules" Academic Press, London, Published 1976.

American Society for Testing Materials (ASTM) Designation: E1164-02, "Standard Practice for Obtaining Spectrometric Data for Object-Color Evaluation," pp. 1-8, published Aug. 2002.

International Organization for Standardization (ISO) International Standard 7724/1, "Paints and Varnishes—Colorimetry—Part 1: Principles," First edition, 1984, 8 pages.

Japanese Industrial Standard, JIS Z 8722, "Methods of Colour Measurement—Reflecting and Transmitting Objects," 2000, 1-57 and 1 correction page, "Errata."

"CIE Publication No. 15.2," *Colorimetry*, Second Edition, 1986, pp. 1-74.

U.S. Appl. No. 11/955,696, filed Dec. 13, 2007, Martin et al., Self-Indicating Wipe for Removing Bacteria from a Surface.

* cited by examiner

WOUND OR SURGICAL DRESSING

BACKGROUND OF THE INVENTION

Wound and surgical dressings are often used to treat, cover and protect wounds and surgical incisions. Wound and surgical dressings come in various forms. For example, for simple cuts, adhesive bandages are typically used. Cotton gauze is also commonly used to cover wounds and surgical incisions. For more serious wounds and surgical incisions, the wound or surgical dressing may include multiple layers of fibrous material with a fluid impervious layer or back sheet to prevent exudates from seeping through the dressing.

Typically, medicaments are often manually applied to the wound or surgical dressing before positioning on a wound or surgical incision. A medicament is a medicinal substance or agent. The medicaments may comprise, for instance, an antimicrobial agent or antibiotic agent to encourage healing. Antiseptics are also commonly applied to prevent infection.

Many medicaments applied to wound or surgical dressings transfer into the wound or surgical incision. Unfortunately, certain individuals may be allergic to many common medicaments, such as antibiotics. Furthermore, there has recently been a push in the medical community to avoid excessive use of antibiotics so as to eliminate the risk that certain bacteria may become resistant to such medications.

As such, a need currently exists for a wound or surgical dressing that removes or prevents the growth of microorganisms, such as bacteria, without leaving substantial amounts of chemicals in the wound or on the surface of the skin. A need also exists for a method of controlling bacterial populations in and around wounds or surgical sites that does not create a risk that the bacteria may develop antimicrobial resistance.

SUMMARY OF THE INVENTION

In general, the present disclosure is directed to a wound or surgical dressing that contains a bacteriostatic composition that is configured to bind or trap any negatively charged matter, such as molecules, particles, microbes, cells, fungi, ions, pathogens, or other microorganisms to a surface of the dressing without releasing substantial amounts of chemicals, such as antimicrobial agents onto the treated area. As used herein, a "bacteriostatic composition" refers to any composition that removes any negatively charged bacteria, pathogens, fungi, microorganisms, ions, molecules or other negatively charged species from a site or any composition capable of inhibiting or retarding the growth of microorganisms.

For example, in one embodiment, the present disclosure is directed to a wound or surgical dressing that comprises a substrate configured to contact or surround a wound or surgical site. A bacteriostatic composition is applied to the substrate. More particularly, the bacteriostatic composition is located on the substrate so as to contact a patient at or near the wound or surgical site. The bacteriostatic composition is bonded to the substrate so that the composition does not substantially transfer to the patient. The bond formed between the bacteriostatic composition and the substrate can vary depending upon various factors and the materials used. The bond, for example, may be a chemical bond such as a covalent bond or an ionic bond or may be a mechanical bond. Any bonding that is capable of substantially preventing the composition from transferring to the patient may be used.

The bacteriostatic composition comprises a chemical compound having a net positive charge for binding with negatively charged matter. For example, the chemical compound can bind to negatively charged molecules, particles, microbes, cells, fungi, ions, pathogens, other microorganisms, and the like. By binding to bacteria, for instance, the bacteriostatic composition not only removes the bacteria from the wound or surgical site but also may inhibit the growth of the bacteria.

The chemical compound contained in the bacteriostatic composition may vary depending upon the particular application. In general, the chemical compound may comprise a cationic polymer, a cationic oligomer such as an inorganic or organic oligomer, or particles, such as particles, coated with the above materials. In particular embodiments, for instance, the chemical compound may comprise a metal based material, such as an aluminum oligomer such as aluminum chlorohydrol or aluminum chlorohydrol. Of particular advantage, aluminum oligomers can form covalent bonds with cellulosic substrates.

In other embodiments, the chemical compound contained in the bacteriostatic composition may comprise an epichlorohydrin-functionalized polyamine, a polyethyleneimine or poly(methacryloxyethyl)trimethylammonium bromide poly (acrylic) acid. In still other embodiments, the bacteriostatic composition comprises particles, such as silica particles, coated with one of the above materials, such as an aluminum oligomer. In an alternative embodiment, the particles may comprise solid aluminum particles or alumina particles. If desired, a binder may be present with the aluminum or the alumina in order to hold the particles together.

The wound or surgical dressing may come in various forms. For example, the dressing may comprise an adhesive bandage, gauze, or a wrap comprising an elastic material. The substrate contained in the wound or surgical dressing that is treated with the bacteriostatic composition may comprise a cellulosic material, such as gauze, an airlaid web, a wetlaid web, a hydroentangled web containing pulp and synthetic fibers, a coform web, and the like. In other embodiments, the substrate may comprise a bonded carded web, a foam, a film, a woven fabric, a knitted fabric, a hydroentangled web containing synthetic fibers only, a meltblown web, a spunbond web, and laminates thereof. For example, in one embodiment, the substrate may comprise a spunbond/meltblown/spunbond laminate.

In still other embodiments, the substrate may comprise an elastic material, such as a stretch-bonded laminate or a neck-bonded laminate.

The bacteriostatic composition may be applied to the entire surface area of the substrate or may only be applied to a certain portion of the substrate. Within the treated area, the amount of bacteriostatic composition may depend upon various factors. In general, for example, the bacteriostatic composition may be applied to the substrate in the treated area in an amount from about 0.01% to about 20% by weight, such as from about 0.05% to about 10% by weight. Once applied to the substrate, the bacteriostatic composition may be crosslinked in order to improve the effectiveness of the bacteriostatic composition or to improve bonding to the substrate.

As described above, the wound or surgical dressing is capable of binding and trapping negatively charged matter and removing the matter from the wound or surgical site. The bacteriostatic composition may also reduce bacterial growth. For example, the wound or surgical dressing treated with the bacteriostatic composition may reduce bacterial growth according to a bacteria binding procedure by at least about 50%, such as at least about 80%, such as at least about 90%.

As stated above, in one embodiment, the substrate may comprise a coform web. Coform webs contain a combination of polymeric fibers and cellulosic fibers. The present inventors have discovered that by treating a coform material with a bacteriostatic composition, the hydrophobicity of the material is greatly increased. Thus, these materials have been found to be very efficient barriers to blood and other biological liquids. Consequently, such materials can be used not only as wound or surgical dressings, but may also be used to produce hospital gowns, surgical drapes, and other medical garments.

In particular, coform materials made according to the present disclosure display increased contact angles to liquids, such as water and blood. For instance, once the coform material is treated with the bacteriostatic composition, the contact angle of the material against various liquids may increase by at least about 10%, such as at least about 20%, such as at least about 30%. For instance, the contact angle of a treated coform material made in accordance with the present disclosure against water may be greater than about 110°, such as greater than about 115°, such as greater than about 120°. When tested against blood, the contact angle of the treated coform material may be greater than about 115°, such as greater than about 118°, such as greater than about 120°.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
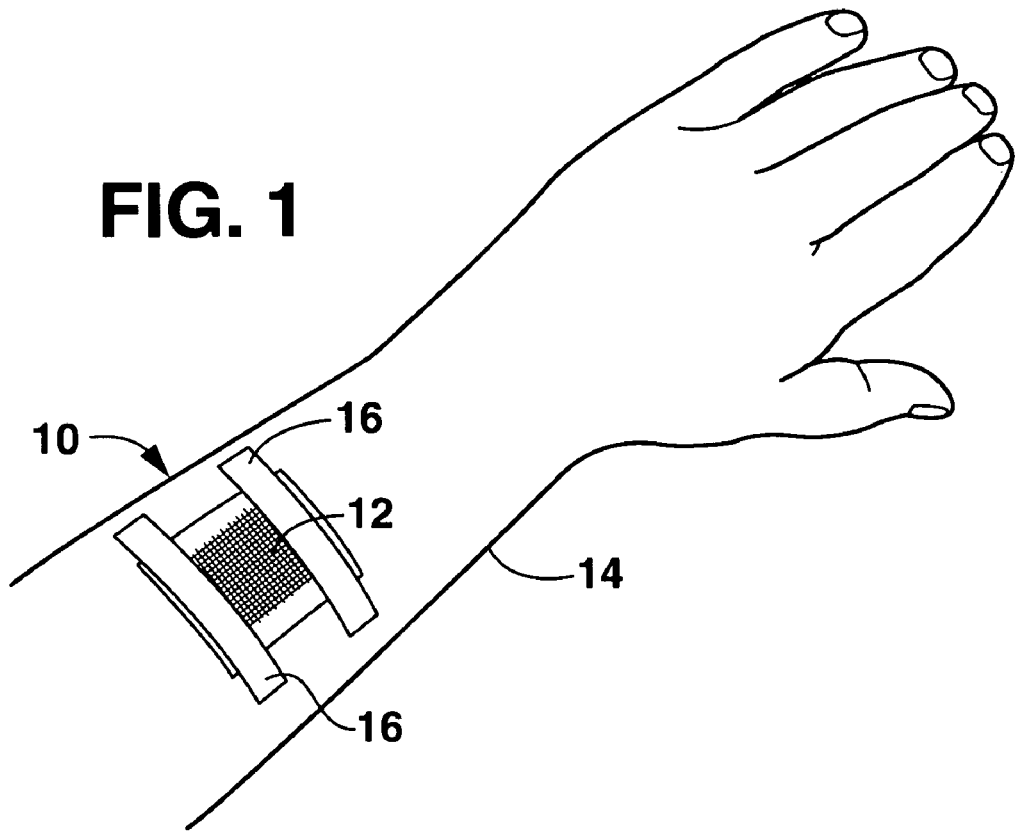
FIG. 1 is a perspective view illustrating one embodiment of a wound or surgical dressing applied to a patient in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

In general, the present disclosure is directed to wound or surgical dressings containing a bacteriostatic composition having a net positive charge. The bacteriostatic composition is bonded to the wound or surgical dressing thus preventing substantial amounts of the composition from transferring to a patient. Due to the net positive charge, the bacteriostatic composition is capable of binding and trapping negatively charged matter, including molecules, particles, microbes, cells, fungi, ions, other microorganisms, pathogens, and the like. In this manner, the bacteriostatic composition not only prevents the negatively charged matter from entering the wound or surgical incision, but can also inhibit the growth of various microorganisms, such as bacteria, as well as removing microorganisms that have already entered the wound.

Of particular advantage, the bacteriostatic composition provides protection to a patient against infection without having to apply chemicals, such as antiseptics or antibiotics, to a patient's skin, wound or surgical incision. When applied to a wound or surgical dressing, for instance, the bacteriostatic composition provides a localized system for removing negatively charged particles or microorganisms without disturbing the wound bed and without interfering with the proteins the patient is synthesizing in order to heal.

Of course, if desired, the wound or surgical dressing of the present disclosure may be used in conjunction with other medicaments. In one particular embodiment, however, no such medicaments are applied directly to the patient. Negatively charged matter, such as bacteria, are thus removed from a wound or surgical incision site through the application of physical means and Coulombic attraction.

In general, the bacteriostatic composition may be applied to any product or article that is intended to be placed over or around a wound, a surgical incision, skin irritations, and the like. The bacteriostatic composition is bonded to a substrate that is contained in the wound or surgical dressing and is located on the substrate so that the composition contacts a patient at or near a wound or surgical site. Wound or surgical dressings that may be treated in accordance with the present disclosure include adhesive bandages, gauze, wrapping materials, or any other products that are used to cover or surround a surgical incision during or after the surgery. The wound or surgical dressing, for instance, may be as simple as a rectangular piece of gauze to a complex multi-layered product designed to treat certain types of wounds or surgical incisions.

The bacteriostatic composition contains a chemical compound having a net positive charge. The chemical compound, for instance, may comprise a cationic polymer, a cationic oligomer, or mixtures thereof. In one embodiment, the bacteriostatic composition may contain particles treated with a cationic compound or polymer. The particular components contained in the bacteriostatic composition may depend upon the particular application and the desired result.

Chemical compounds that may be incorporated into the bacteriostatic composition may include, for instance, cationic polymers, cationic oligomers, mixtures thereof, and particles that are coated with the above cationic materials. In general, any suitable positively charged material may be incorporated into the bacteriostatic composition that is capable of being bonded to the wound or surgical dressing.

In one particular embodiment, for instance, a cationic oligomer may be incorporated into the bacteriostatic composition. The cationic oligomer may comprise an organic or inorganic oligomer. For instance, examples of inorganic oligomers include aluminum oligomers. Aluminum oligomers may include, for instance, aluminum chlorohydrol and aluminum chlorohydrate. Aluminum chlorohydrate can be represented as follows: $Al_2(OH)_{6-n}Cl_n$, wherein n can be from 1 to 5.

In addition to the above, any suitable compound, such as a metal ion or complex, positively charged polymer, molecule, etc. possessing sufficient positive charge may be used and incorporated into the bacteriostatic composition. Further, in addition to aluminum oligomers, various other positively charged aluminum compounds may be used. For instance, any suitable aluminum salt may be present in the bacteriostatic composition, such as aluminum sulfate or alum.

Cationic polymers that may be used in the bacteriostatic composition include, for instance, polyethyleneimine, high charged density polyelectrolites such as poly(methacryloxyethyl)trimethylammonium bromide poly(acrylic) acid and epichlorohydrin-functionalized polyamines. Such polymers are commercially available from Hercules Inc., of Wilmington, Del. under the tradenames KYMENE®, and RETEN®, from National Starch and Chemical Company of Bridgewater, N.J. under the tradename COBOND® and from Calgon Polymers of Pittsburgh, Pa.

In still another embodiment, the bacteriostatic composition may contain cationic particles or particles coated with a cationic material. For instance, the bacteriostatic composition may contain small particles, such as nanoparticles, coated with an aluminum oligomer. The particles may comprise, for instance, silica particles or alumina particles. Particles coated with aluminum chlorohydrate, for example, are available from Nissan Chemicals, Inc. of Houston, Tex. under the tradename SNOWTEX.

In addition to coated particles, positively charged aluminum particles or alumina particles may be used. The particles may be made exclusively from the above materials or may contain a binder if desired.

In addition to the above materials, it should be understood that any other suitable cationic material that is capable of bonding or being bonded to a wound or surgical dressing may be used in the bacteriostatic composition of the present disclosure. Desirably, the positively charged materials are mild on the skin, are not appreciably antimicrobial in nature, and do not leach substantially once bonded to the surface of a substrate.

As described above, the bacteristatic composition may be applied to any suitable wound or surgical dressing that is configured to contact or surround a wound, a surgical incision, or any skin irritation. When applied to a wound or surgical dressing, the bacteriostatic composition is bonded chemically or mechanically to a substrate on the dressing that is intended to contact a patient at or near the wound or surgical site. The substrate can be made from any suitable material. For example, the bacteriostatic composition may be bonded to a substrate made from natural materials or a substrate made from synthetic materials. For exemplary purposes, the following are some materials that may be used to bond with the bacteriostatic composition.

In one embodiment, various substrates containing cellulosic material may be used in accordance with the present disclosure. Of particular advantage, cellulosic materials are capable of forming chemical bonds with cationic materials having hydroxy groups. Examples of cellulosic materials include gauze, wetlaid tissue webs, and airlaid webs.

Wetlaid tissue webs generally refer to tissue webs made from an aqueous suspension of cellulosic, namely pulp fibers. The pulp fibers may comprise, for instance, softwood fibers, hardwood fibers, and mixtures thereof. The wet pressed tissue product can generally be formed in any of a variety of processes known in the art. For example, the tissue web may be made through adhesive creping, wet creping, double creping, embossing, wet pressing, air pressing, through-air drying, creped through-air drying, uncreped through-air drying, as well as other steps known in the art.

Airlaid webs, on the other hand, are formed in an air forming process in which a fibrous nonwoven layer is created. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air or a spray adhesive. The production of airlaid nonwoven composites is well defined in the literature and documented in the art. Examples include the DanWeb process as described in U.S. Pat. No. 4,640,810 to Laursen et al. and assigned to Scan Web of North America Inc, the Kroyer process as described in U.S. Pat. No. 4,494,278 to Kroyer et al. and U.S. Pat. No. 5,527,171 to Soerensen assigned to Niro Separation a/s, the method of U.S. Pat. No. 4,375,448 to Appel et al assigned to Kimberly-Clark Corporation, or other similar methods.

Other materials containing cellulosic fibers include coform webs and hydroentangled webs. In the coform process, at least one meltblown diehead is arranged near a chute through which other materials are added to a meltblown web while it is forming. Such other materials may be natural fibers, superabsorbent particles, natural polymer fibers (for example, rayon) and/or synthetic polymer fibers (for example, polypropylene or polyester), for example, where the fibers may be of staple length.

Coform processes are shown in commonly assigned U.S. Pat. No. 4,818,464 to Lau and U.S. Pat. No. 4,100,324 to Anderson et al., which are incorporated herein by reference. Webs produced by the coform process are generally referred to as coform materials. Natural fibers that may be combined with the meltblown fibers include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Acordis Cellulose Fibers Incorporated of Axis, Ala.

When containing cellulosic materials such as pulp fibers, a coform material may contain the cellulosic material in an amount from about 10% by weight to about 80% by weight, such as from about 30% by weight to about 70% by weight. For example, in one embodiment, a coform material may be produced containing pulp fibers in an amount from about 40% by weight to about 60% by weight.

Once a coform material is treated with a bacteriostatic composition in accordance with the present disclosure, in one embodiment, the bacteriostatic composition may bond to the cellulosic material contained within the coform material. Of particular advantage, the present inventors discovered that when certain coform materials are treated with a bacteriostatic composition, the hydrophobicity of the material may be increased. Due to the increased hydrophobicity, the barrier properties of the material are improved.

In addition to coform webs, hydroentangled webs can also contain synthetic and pulp fibers. Hydroentangled webs refer to webs that have been subjected to columnar jets of a fluid that cause the fibers in the web to entangle. Hydroentangling a web typically increases the strength of the web. In one embodiment, pulp fibers can be hydroentangled into a continuous filament material, such as a spunbond web. The hydroentangled resulting nonwoven composite may contain pulp fibers in an amount from about 50% to about 80% by weight, such as in an amount of about 70% by weight. Commercially available hydroentangled composite webs as described above are commercially available from the Kimberly-Clark Corporation under the name HYDROKNIT. Hydraulic entangling is described in, for example, U.S. Pat. No. 5,389,202 to Everhart, which is incorporated herein by reference.

In addition to the above substrates containing cellulosic fibers, other substrates that may be used in accordance with the present disclosure include synthetic webs. For instance, the substrate may comprise a meltblown web, a spunbond web, and laminates thereof.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited on a collecting surface.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

Laminates containing meltblown webs and spunbond webs include, for instance, meltblown/spunbond laminates and spunbond/meltblown/spunbond laminates.

In one embodiment, the synthetic webs may be elastic. As used herein, the terms "elastic" and "elastomeric" are generally used to refer to materials that, upon application of a force, are stretchable to a stretched, biased length which is at least about 125%, or one and one fourth times, unstretched length, and which will retract at least about 50% of its elongation upon release of the stretching, biasing force.

Elastic laminates that may be used as the substrate include, for instance, neck-bonded laminates and stretch-bonded laminates. As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992, 4,981,747, 4,965,122, and 5,336,545, all to Morman, all of which are incorporated herein by reference thereto.

As used herein, the term "stretch-bonded laminate" refers to a composite material having at least two layers in which one layer is a nonelastic gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen et al., which is incorporated herein by reference. Other composite elastic materials are described and disclosed in U.S. Pat. No. 4,789,699 to Kieffer et al., U.S. Pat. No. 4,781,966 to Taylor, U.S. Pat. No. 4,657,802 to Morman, and U.S. Pat. No. 4,655,760 to Morman et al., all of which are incorporated herein by reference thereto.

In still another embodiment, the substrate may comprise a spunlace fabric. Spunlace fabrics are made according to a hydroentanglement process. The spunlace process subjects the fiber web to fine jets of water at high pressures. When the water streams contact the web, it repositions and entangles the fibers into an interlocked "spunlace" web. The web is then dried in hot ovens. Generally speaking, spunlace webs contain no chemical binders, and they have an excellent textile-like drape and softness; good mechanical and aesthetic properties, and good absorbency and wetting. A wide range of natural and synthetic fibers can be used to make spunlace webs, including polypropylene, Rayon, PET, and nylon. Staple fibers are also used in spunlace nonwovens products. Spunlace fabrics may include, for instance, a combination of rayon fibers and polyester fibers. The spunlaced fabrics may be creped or uncreped.

In still another embodiment, bonded carded webs may be used in the wound or surgical dressing as a substrate to bond to the bacteriostatic composition.

"Bonded carded webs" refer to webs which are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

In still other embodiments, the substrate may comprise a foam, such as a polyurethane foam or a film. The film can be made from any suitable polymeric material. In still other embodiments, the substrate may comprise a woven fabric or a knitted fabric. The woven or knitted fabric may be made from natural fibers or synthetic fibers.

Figure 2:
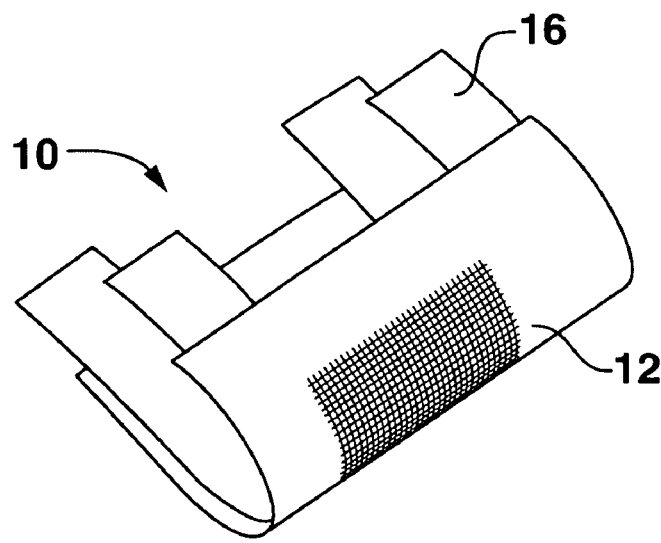
FIG. 2 is another perspective view of the wound or surgical dressing illustrated in FIG. 1.

Referring now to the figures, various articles that may be made in accordance with the present disclosure are shown. For example, referring to FIGS. 1 and 2, a wound or surgical dressing generally 10 is shown comprising a substrate 12 made from gauze. In FIG. 1, the wound or surgical dressing 10 is shown applied to a patient 14. In order to apply the gauze 12 to the skin of the patient, adhesive tape 16 is used. In other embodiments, the adhesive tape 16 may be formed integral with the gauze. For example, the adhesive tape may completely surround the gauze forming an adhesive perimeter.

In accordance with the present disclosure, a bacteriostatic composition is applied to the surface of the gauze 12 that is intended to contact the patient 14. The bacteriostatic composition is bonded to the gauze either chemically or mechanically and is configured to bind and trap any negatively charged matter that it comes into contact with. Negatively charged matter, for instance, may comprise bacteria, pathogens, fungi, other microorganisms, ions, molecules and the like.

Figure 3:
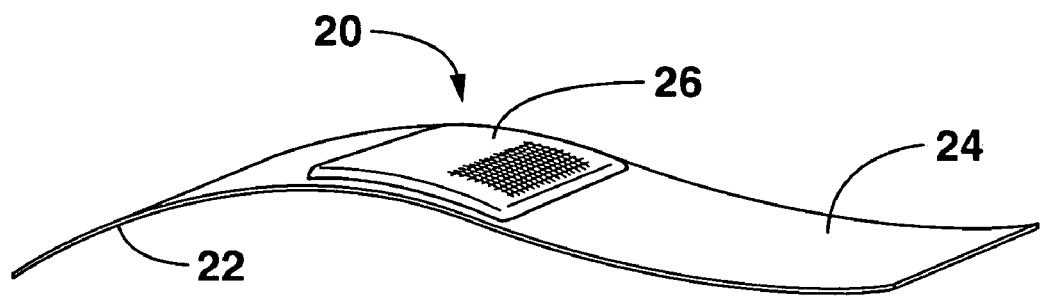
FIG. 3 is a perspective view of another embodiment of a wound or surgical dressing made in accordance with the present disclosure.

Referring to FIG. 3, another embodiment of a wound or surgical dressing is shown. In this embodiment, the wound or surgical dressing comprises an adhesive bandage generally 20. The adhesive bandage 20 includes a base layer 22 which is the layer seen by the consumer following application of the bandage to a wound. The base layer, for example, may be formed from a polymeric material, such as a nonwoven sheet or a film. Nonwoven sheets may comprise meltblown webs and/or spunbond webs. The base layer 22 may be perforated in order to provide for some level of flexibility and breathability.

A skin-friendly adhesive 24 is usually placed over the bottom surface of the base layer 22.

The adhesive bandage 20 further includes a substrate 26 that is positioned in the center of the base layer 22. The substrate 26 typically comprises an absorbent pad. The absorbent pad can be made from any of the materials described above.

During packaging, the adhesive bandage 20 may also include various non-stick layers that protect the adhesive prior to use.

In accordance with the present disclosure, a bacteriostatic composition may be applied to the absorbent layer 26 for contact with the skin of a patient. The bacteriostatic composition is capable of trapping and binding to bacteria and other negatively charged materials.

Figure 4:
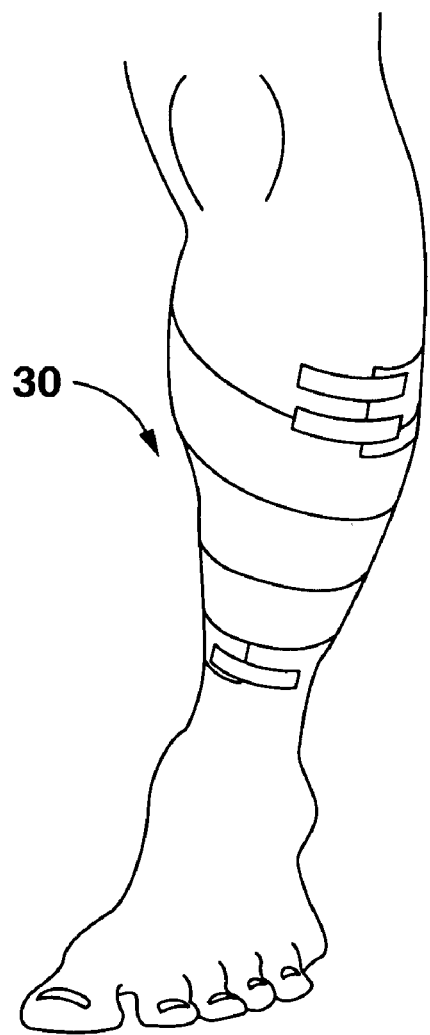
FIG. 4 is a perspective view of still another embodiment of a wound or surgical dressing made in accordance with the present disclosure.

Referring to FIG. 4, still another embodiment of a wound or surgical dressing made in accordance with the present disclosure is shown. In this embodiment, the wound or surgical dressing comprises a wrapping 30. As illustrated, the wrapping 30 is shown wrapped around the leg of a patient in a spiral manner.

Such wrapping materials can be made from any of the materials described above. In one embodiment, for instance, the wrapping may comprise an elastic laminate, such as a stretch-bonded laminate or a neck-bonded laminate. In accordance with the present disclosure, a bacteriostatic composition may be applied to the wrapping over the entire surface of the wrapping or over a portion of the wrapping that is intended to contact the skin of a patient.

In order to bond the bacteriostatic composition to a substrate contained in a wound or surgical dressing, various techniques and processes may be used. The composition may be adhered to the substrate using chemical bonds or mechanical bonds. Bonding can be accomplished in a number of ways. The composition may bond to the substrate directly or an auxiliary agent may be used to bond the composition to the substrate.

The bacteriostatic composition may be applied to the substrate using various methods. In general, the bacteriostatic composition is contained in a liquid carrier, such as water or a solvent and then applied to the substrate. For example, the bacteriostatic composition may be applied using traditional dip and squeeze techniques, where the substrate is dipped into the composition and excess liquids are squeezed off. In alternative embodiments, the bacteriostatic composition may be applied to the substrate using brush coating, spraying, inkjet printing, and the like. It is also possible to add the bacteriostatic composition as an internal treatment to, for instance, a polymer fiber.

In another embodiment, the bacteriostatic composition may be first applied to a cellulosic material prior to incorporating the cellulosic material into a nonwoven web. For example, in one embodiment, the bacteriostatic composition may be combined with pulp fibers in an aqueous suspension prior to forming a tissue web. Alternatively, the bacteriostatic composition may be combined with the pulp fibers and then dried prior to being incorporated into an airlaid web, a coform web, or a hydroentangled web.

In one embodiment, the bacteriostatic composition may crosslink once applied to the substrate. For instance, once applied to the substrate, the substrate may be treated with heat at a temperature and for a time sufficient to crosslink the coating and adhere it to the web. The crosslinking process for functionalized cationically charged polymers involves reaction between crosslinkable functional groups (e.g., epoxy group) of the coating with either another functional group of the coating (e.g., hydroxyl group) or with a substrate functional group. For example, the substrate could be cellulose where hydroxyl groups of the fibers would intermoleculady crosslink with epoxy groups of the coating. In the case of alumina oligomers, the crosslinking process involves Al—OH groups of the oligomer and OH groups from either the oligomer (intramolecular crosslinking) or OH groups from the substrate (intermolecular crosslinking). It's believed that particles coated with alumina oligomer would adhere to OH-containing surfaces by crosslinking the OH group with Al—OH groups of the oligomer.

The combination of time and temperature sufficient to crosslink the polymer will depend on the polymer and substrate chosen. In one embodiment, for instance, ambient temperatures may be sufficient to cause the polymer to crosslink. In other embodiments, however, the web may be heated in order to cause crosslinking. When heated, for instance, the substrate may be heated to a temperature of from about 50° C. to about 300° C., such as from about 90° C. to about 125° C.

Depending on the nature of the fibers, functionlized polymers (such as KYMENE® polymers containing epoxy groups) are capable of involving both intra-molecular (i.e., only within the coating layer) and inter-molecular (i.e., only with the substrate) crosslinking processes. It is believed to be likely that the crosslinking process will combine both intramolecular and intermolecular processes if the substrates are functionalized. Alternatively, if the substrate is not capable of participating in the chemical crosslinking process, then only intramolecular crosslinking may occur. In either case, a durable coating is often obtained when the non-functionalized substrate is made wettable by pre-treating before coating. The term "bonding to the substrate" includes, therefore, instances of intramolecular crosslinking that create a "sleeve" around the fibrous substrate, as well as intermolecular crosslinking where the chemical or a carrier of the chemical (such as a nanoparticle coated with an alumina oligomer) forms a covalent bond on the substrate, and combinations thereof. A cationically charged chemical "bonds to the substrate" if it does not leach from the substrate during use, where "not leach" from a substrate means that the concentration of the chemical in the liquid left on a surface with which the substrate comes into contact with, is less than the critical concentration for the chemical to have antimicrobial properties.

Alternatively, the cationically charged compound may be imbedded in a product made from fibers by melt-extruding the fiber-forming polymer containing a desired amount of the cationically charged compound as an additive in the fibers of the web. Such compounds may "bloom" to the surface when the web is exposed to hydrophilic solvents such as water. These melt extrudable fibers may contain a polyolefin and a cationically charged compound. The cationically charged compound may also contain a chemical segment (i.e., compatibilizer) that is soluble in the polyolefin such that the salt is compatibilized with the polymer. The cationically charged chemicals may be, for example, amphiphilic quaternium ammonium salts that are compatible with hydrophobic webs, examples of which are taught by Nohr and Macdonald in U.S. Pat. No. 5,853,883, which is incorporated herein by reference. If the hydrophobic segment of the salt that is compatible with the hydrophobic polymer is relatively large (with respect to the ionic segment of the salt) such that the amount of salt that leaches out of the web is insufficient to kill bacteria, then the web does not have antimicrobial activity. The cationically charged groups generally come to the surface of the predominately polymeric fibers when the web is exposed to water. Such blooming gives the webs properties similar to those of substrates coated with cationically charged compounds.

The amount of bacteriostatic composition applied to the substrate may vary and depends on numerous factors. The amount applied, for instance, depends upon the ingredients contained in the bacteriostatic composition, the material used to form the substrate, and the amount of bonding that can occur between the composition and the substrate. Other factors include the desired amount of activity needed on the wound or surgical dressing and the type of wound or incision site that may be treated.

In general, when applied to a substrate, the bacteriostatic composition may be applied in a treated area in an amount from about 0.01% to about 20% by weight, such as from about 0.05% to about 10% by weight. In still other embodiments, the bacteriostatic composition may be applied to the substrate in a treated area in an amount from about 5% to about 8% by weight.

As described above, the bacteriostatic composition traps and binds negatively charged materials, thus removing them from the surface of the patient. For instance, when applied to a substrate, the bacteriostatic composition may reduce bacterial growth according to a bacteria binding procedure by at least about 50%, such as at least about 75%. In other embodiments, for instance, the treated substrate may reduce bacterial growth by at least about 80%, such as by at least about 90%.

The present invention may be better understood with reference to the following examples.

Example 1

In order to determine the effect against bacteria of an aluminum chlorohydrate treated material, an assay was designed that measured the growth of *E. coli* in material treated with the aluminum chlorohydrate. The assay procedure is as follows.

An *E. coli* solution in PBS (100 µL of $10^4$ cells/mL) was added to treated and untreated VIVA® paper towels available commercially from the Kimberly-Clark Corporation and wire textured coform laminates (WTCL). The materials were then placed in 4 mL of media containing ampicillin. The cultures were shaken overnight at 37° C. to see if the materials would inhibit cell growth.

The following day the absorbance was measured at 590 nm and 650 nm to estimate cell growth.

| Material | A@590 nm | A@650 nm |
|---|---|---|
| Media | 0.035, 0.034 | 0.064, 0.041 |
| Positive control | 0.361, 0.332 | 0.386, 0.364 |
| VIVA ® Paper Towel | 0.039, 0.039 | 0.089, 0.084 |
| VIVA ® Paper Towel + *E. coli* | 0.207, 0.209 | 0.254, 0.251 |
| VIVA ® Paper Towel Al | 0.036, 0.036 | 0.074, 0.044 |
| VIVA ® Paper Towel Al + *E. coli* | 0.038, 0.037 | 0.047, 0.049 |
| WTCL | 0.038, 0.037 | 0.047, 0.049 |
| WTCL + *E. coli* | 0.138, 0.147 | 0.196, 0.215 |
| WTCL Al | 0.045, 0.038 | 0.084, 0.116 |
| WTCL Al + *E. coli* | 0.104, 0.117 | 0.155, 0.213 |

As can be seen from the results, the aluminum chlorohydrate treated VIVA® paper towels inhibited *E. coli* growth in this experiment as evidenced by the decrease in absorbance at 590 and 650 nm.

Example 2

The above experiment was repeated as described by adding 100 µL of $10^4$ cells/mL *E. coli* solution or PBS onto treated and untreated materials. The materials were then placed in 3 mL of media containing ampicillin. The cultures were shaken overnight at 37° C. to see if the materials would inhibit cell growth.

The materials tested included VIVA® paper towels and uncreped through-air dried (UCTAD) paper towels.

The absorbance at 590 nm was measured, and aliquots were removed for serial dilutions for plating for most of the samples.

| Material | Mass (mg) | A 590 nm | A 590 nm | Colony Counts* | Cells/mL |
|---|---|---|---|---|---|
| PBS in media (negative control) | | 0.042, 0.042 | | | |
| 100 µL of $10^4$ cells/mL | | 0.564, 0.616 | | | |
| VIVA ® Paper Towel | 134, 115 | 0.210, 0.236 | 0.234, 0.242 | 77, 98, 164, 162 | $1.3 \times 10^9$ |
| VIVA ® Paper Towel 0.5% | 107, 105 | 0.143, 0.138 | 0.089, 0.084 | 1644, 1548, 1040, 1160 | $1.3 \times 10^8$ |
| VIVA ® Paper Towel 1% | 113, 123 | 0.081, 0.071 | 0.073, 0.075 | 693, 713, 1110, 1075 | $9.0 \times 10^7$ |
| VIVA ® Paper Towel 1% (not washed) | 116, 107 | 0.065, 0.074 | 0.073, 0.083 | 233, 251, 478, 537 | $3.8 \times 10^7$ |
| UCTAD Paper Towel | 98, 106 | 0.205, 0.211 | 0.167, 0.160 | 374, 388, 94, 112 | $2.4 \times 10^9$ |
| UCTAD Paper Towel 1% | 111, 119 | 0.090, 0.088 | 0.093, 0.094 | 1069, 1092, 1276, 1317 | $1.2 \times 10^8$ |

*Colonies from a dilution of $10^7$ (untreated materials) or $10^5$ (treated materials).

Both treated UCTAD and treated VIVA® paper towels showed inhibition of cell growth (10-100 fold difference) in this experiment compared to their untreated controls. These data show that cellulosic materials treated with aluminum chlorohydrate can inhibit cell growth.

Example 3

In order to test the ability of a material treated with the aluminum chlorohydrate to attract anions, experiments were designed to determine how a negatively charged liquid will interact with both treated and untreated materials.

A piece of gauze was treated with aluminum chlorohydrate by dipping the material into a 1 wt % solution of the compound, squeezing out the excess liquid, and then drying the gauze at about 80° C. for 20 minutes. The gauze was then rinsed with deionized water, and the excess liquid was squeezed out. The gauze was dried at 80° C. for 20 minutes.

A piece of untreated gauze and a piece of treated gauze were tested by forcing a 0.1 wt % solution of FD&C Blue #1 into each piece of material, using a pipette. Five microliters of the anionic dye solution was put into each piece of gauze in multiple places. Each piece of gauze was rinsed copiously with water.

The dye remained in the treated gauze, and more specifically in the areas that the dye was forced into the material. In the untreated gauze, the dye migrated throughout the gauze. The results of the experiment show that the aluminum chlorohydrate treatment enables the gauze to effectively trap anions.

Example 4

Again, pieces of treated and untreated gauze were tested to compare how each material reacts to anionic liquids. Each piece of gauze was laid flat, and liquid was gently applied to the surface. A clock was started as the first drop of liquid was distributed onto the gauze. Initially, the liquids applied to the treated gauze remained on the surface of the material. The liquids were as follows:
FD&C blue #1 in water
1 mg/mL beta-casein in water w/FD&C Green #3
Whole blood with anticoagulant After 30 minutes, the droplets had not wet through the treated gauze; however, the liquid had dispersed throughout the untreated gauze. This implies that the treatment is resistant to protein deposition.

Example 5

The liquids used in the previous experiment were then forced into new pieces of treated and untreated gauze. The pieces of material were rinsed with water.

In the treated gauze the liquid remained in the areas that it was first introduced, even after the rinsing. The liquids dispersed throughout the untreated gauze.

Example 6

In order to determine how efficient the treatment is in holding bacteria, the following test procedure was carried out.

Two by two inch (5 by 5 cm) squares of materials were cut and weighed in duplicate. Serial dilutions of an ampicillin-resistant *E. Coli* solution were made to achieve a final concentration of ~$10^5$ cells per mL. One hundred microliters of sterile PBS were added to each material. After 5 minutes, one hundred microliters of the bacteria solution were added onto each material. The materials were removed and placed into 10 mL of sterile PBS in 50 mL tubes. The tubes were sonicated (5 cycles of 30 seconds on, 30 seconds off) in a water bath to dislodge any bacteria that is not bound tightly to the material. One hundred microliters of the PBS solution from the tubes containing the material were plated in duplicate onto LB agar plates containing ampicillin. The plates were incubated at 37° C. and bacterial colonies were counted the following day. Data is shown as the percentage of reduction of bacteria in solution as compared to the PBS control.

The following materials were tested:

WYPALL® X80 material: WYPALL® materials are also available from Kimberly-Clark Corporation. WYPALL® X80 material is a highly absorbent, bulky HYDROKNIT® material having high wet strength and capacity. The materials tested herein had a basis weight of 125 gsm and were made from 75 weight percent pulp and 25 weight percent polypropylene spunbond fibers.

Textured coform laminate (TCL): This material was an elastic laminate having outer layers on either side of a core. The outer layers had a basis weight of 35 grams per square meter (gsm) each and made according to the coform process, from a blend of 60 weight percent CF405 fiberized southern softwood pulp from Weyerhauser Corp. and 40 weight percent PF-105 polypropylene meltblown fibers from Basell Polyolefins Company N.V. of Hoofddorp, the Netherlands. The core was 30 gsm in basis weight and made of filaments and nonwoven fabric. The filaments comprised 70 weight percent of the core and were made from AFFINITY® metallocene-based polyethylene from the Dow Chemical Company of Midland, Mich., USA. The nonwoven fabric was made according to the meltblown process from 80 weight percent AFFINITY® polyethylene, 15 weight percent REGALREZ® 1126 hydrocarbon resin from Eastman Chemical Company of Kingsport, Tenn., USA and 5 weight percent DNDB 1077 linear low density polyethylene from the Dow Chemical Company.

VIVA® Scrub Cloth: This material is a cellulosic paper towel and is available from the Kimberly-Clark Corporation. It has a printed polyethylene acetate binder on both sides of the base-sheet which is composed of 72 weight percent softwood bleached kraft, 13 weight percent polyethylene vinyl acetate binder, 11 weight percent synthetic (polyester) fiber, 3 weight percent hardwood kraft, 1 weight percent total nitrogen.

Airlaid Fabric:

The airlaid materials tested herein were made from 83 weight percent Weyerhaeuser CF405 pulp, and 17 weight percent latex binder (National Starch Dur-O-Set Elite PE) and had a basis weight of 68 gsm.

The following treatments were applied to the above materials:

KYMENE® 2064: A 0.1 weight percent KYMENE® 2064 solution was prepared by diluting a stock KYMENE® 2064 (from Hercules Inc., Wilmington, Del., USA) solution (20 weight percent solution in water, 5 mL) with de-ionized water (995 mL). KYMENE® 2064 was "activated" by adjusting the solution pH with NaOH (0.4 M), which was measured at 8.8. Treatment of the substrates entailed a "dip and squeeze" protocol. Each substrate was submerged in the 0.1 weight percent KYMENE® 2064 solution and agitated for approximately 1 minute to ensure saturation. The treated material was then squeezed to remove excess treatment solution using an Atlas Laboratory Wringer Type LW-1 (Atlas Electrical Devices Co., Chicago, Ill., USA) equipped with a 5 lb weight for the squeeze pressure. The material was cured at 100° C. for 20 minutes, allowed to cool to room temperature, and washed twice with de-ionized water. Excess water was removed using the same "dip and squeeze" protocol above. The washed material was allowed to dry at 100° C. for 30 minutes.

KYMENE® 450: A 0.1 weight percent KYMENE® 450 solution was prepared by diluting a stock KYMENE® 450 (Hercules Inc.) solution (20 weight percent solution in water, 5 mL) with de-ionized water (995 mL). KYMENE® 450 was "activated" by adjusting the solution pH with NaOH (0.4 M), which was measured at 9.2. Treatment of the substrates was performed in the same manner as with KYMENE® 2064 above.

KYMENE® 557 LX: A 0.1 weight percent KYMENE® 557 LX solution was prepared by diluting a stock KYMENE® 557 LX (Hercules Inc.) solution (12.5 weight percent solution in water, 8 mL) with de-ionized water (992 mL). The solution pH was adjusted with NaOH (0.4 M), which was measured at 8.0. Treatment of the substrates was performed in the same manner as with KYMENE® 2064 above.

Alumina oligomer (aluminium chlorohydrol, aluminum chlorohydrate): A 1 weight percent alumina oligomer solution was prepared by diluting a stock alumina oligomer (from GEO Specialty Chemicals, Little Rock, Ark., USA) solution (50 weight percent solution in water, 20 mL) with de-ionized water (980 mL). The measured pH was 4.6. Treatment of the substrates entailed a "dip and squeeze" protocol. Each substrate was submerged in the 1 weight percent alumina oligomer solution and agitated for approximately 1 min to ensure saturation. The treated material was then squeezed to remove excess treatment solution using an Atlas Laboratory Wringer Type LW-1 (Atlas Electrical Devices Co.) equipped with a 5 lb weight for the squeeze pressure. The material was heated at 100° C. for 20 minutes, allowed to cool to room temperature, and washed twice with de-ionized water. Excess water was removed using the same "dip and squeeze" protocol above. The material was allowed to dry at 100° C. for 30 minutes.

SNOWTEX® AK nanoparticle (alumina-coated silica particles): A 1 weight percent SNOWTEX® AK nanoparticle solution was prepared by diluting a stock SNOWTEX® AK nanoparticle (from Nissan Chemicals Ltd, Houston, Tex., USA) solution (20 weight percent solution in water, 75 mL) with de-ionized water (1425 mL). The measured pH was 4.0. Treatment of the substrates entailed a "dip and squeeze" protocol. Each substrate was submerged in 1 weight percent SNOWTEX® AK nanoparticle solution and agitated for approximately 1 min to ensure saturation. The treatment solution for each substrate was not recycled for subsequent treatments. The treated material was then squeezed to remove excess treatment solution using an Atlas Laboratory Wringer Type LW-1 (Atlas Electrical Devices Co.) equipped with a 5 lb weight for the squeeze pressure. The material was heated at 100° C. for 20 minutes, allowed to cool to room temperature, and washed twice with de-ionized water. Excess water was removed using the same "dip and squeeze" protocol above. The material was allowed to dry at 100° C. for 30 minutes.

The following results were obtained:

| Material | Treatment | Reduction of Bacteria in Solution (%) N = 4 |
|---|---|---|
| PBS control | — | 0 |
| WYPALL ® X80 Wiper | — | 62 |
| WYPALL ® X80 Wiper | KYMENE ® 2064 | 72 |
| WYPALL ® X80 Wiper | KYMENE ® 450 | 63 |
| WYPALL ® X80 Wiper | KYMENE ® 557 | 40 |
| WYPALL ® X80 Wiper | Al oligomer | 84 |
| WYPALL ® X80 Wiper | SNOWTEX ® AK nanoparticle | 84 |
| TCL | — | 47 |
| TCL | KYMENE ® 2064 | 77 |
| TCL | KYMENE ® 450 | 70 |
| TCL | KYMENE ® 557 | 41 |
| TCL* | Al oligomer | 94, 97 |
| TCL | SNOWTEX ® AK nanoparticle | 95 |
| VIVA ® Scrub Cloth* | — | 58, 48 |
| VIVA ® Scrub Cloth* | KYMENE ® 2064 | 83, 73, 78 |
| VIVA ® Scrub Cloth | KYMENE ® 450 | 59 |
| VIVA ® Scrub Cloth | KYMENE ® 557 | 80 |
| VIVA ® Scrub Cloth | Al oligomer | 82 |
| VIVA ® Scrub Cloth | SNOWTEX ® AK nanoparticle | 68 |
| Airlaid | — | 10 |
| Airlaid | KYMENE ® 2064 | 64 |
| Airlaid | KYMENE ® 450 | 67 |
| Airlaid | KYMENE ® 557 | 36 |
| Airlaid | Al oligomer | 75 |
| Airlaid | SNOWTEX ® AK nanoparticle | 57 |

*Materials tested multiple times

All materials, treated and untreated, showed a reduction in bacteria in the PBS solution after sonication. The most dramatic results are found in materials treated with KYMENE® 2064, KYMENE® 450, the aluminum oligomer, and in some cases, the SNOWTEX® AK nanoparticle particles. In all cases except for the WYPALL® material, the treated materials showed a larger reduction in bacteria in solution than the untreated materials. It is desirable that the treated materials reduce bacterial growth according to this bacteria binding procedure by at least 50 percent, more desirably by at least 75 percent and still more desirably by at least 90 percent.

Example 7

When an electrolyte solution is forced through a porous plug of material, a streaming potential develops due to the motion of ions in the diffusion layer which can be measured by an Electro Kinetic Analyzer (from Brookhaven Instruments Corporation, Holtsville, N.Y., USA). This value is then used to calculate the zeta potential according to the formula published by D. Fairhurst and V. Ribitsch (Particle Size Distribution II, Assessment and Characterization, Chapter 22, ACS Symposium Series 472, Edited by Provder, Theodore, ISBN 0841221170).

During the sample preparation, treated and untreated substrates were cut to two identical pieces (120 mm×50 mm) and then placed into the sample cell with TEFLON® spacers between them. After the sample cell was mounted onto the instrument, all the air bubbles were removed by purging. Then KCl solution (1 mM, pH=5.9, Temp=22° C.) was forced through the two layers of the media and Ag/AgCl electrodes were used to measure the streaming potential. All samples were tested under similar pH, solution conductivity and using the same number of spacers.

The materials tested and the treatments applied to the materials are described in Example 6 above.

Each testing was repeated 4 times, and the results are summarized in table below.

| Material | Treatment | Streaming Zeta Potential (mV) |
|---|---|---|
| WYPALL ® X80 Wiper | — | −1 |
| WYPALL ® X80 Wiper | KYMENE ® 2064 | +11 |
| WYPALL ® X80 Wiper | KYMENE ® 450 | +12 |
| WYPALL ® X80 Wiper | KYMENE ® 557 | +5 |
| WYPALL ® X80 Wiper | Al oligomer | +8 |
| WYPALL ® X80 Wiper | SNOWTEX ® AK | +25 |
| TCL | — | −2 |
| TCL | KYMENE ® 2064 | +29 |
| TCL | KYMENE ® 450 | +33 |
| TCL | KYMENE ® 557 | +15 |
| TCL* | Al oligomer | +25 |
| TCL | SNOWTEX ® AK | +27 |
| VIVA ® Scrub Cloth* | — | −11 |
| VIVA ® Scrub Cloth* | KYMENE ® 2064 | +23 |
| VIVA ® Scrub Cloth | KYMENE ® 450 | +22 |
| VIVA ® Scrub Cloth | KYMENE ® 557 | +11 |
| VIVA ® Scrub Cloth | Al oligomer | +7.3 |
| VIVA ® Scrub Cloth | SNOWTEX ® AK | +13 |
| Airlaid | — | −6 |
| Airlaid | KYMENE ® 2064 | +40 |
| Airlaid | KYMENE ® 450 | +38 |
| Airlaid | KYMENE ® 557 | +31 |
| Airlaid | Al oligomer | +17 |
| Airlaid | SNOWTEX ® AK | +25 |

As can be seen from the data, the zeta potential for untreated substrates was negative, ranging from −11 mV to −1 mV at pH ~5.9. The negative values for the untreated substrates indicate there should be repulsion between most bacteria and the untreated substrates. After treatment, the zeta potential for all the substrates became positive. The most cationically charged substrates are found to be materials treated with KYMENE® 2064, KYMENE® 450, the aluminum oligomer, and SNOWTEX® AK particles.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A wound or surgical dressing comprising:
   a substrate configured to contact or surround a wound or surgical site, wherein the substrate comprises cellulosic fibers; and
   a chemical compound covalently bonded to the cellulosic fibers of the substrate and being located on the substrate so as to contact a patient at or near a wound or surgical site, wherein the covalent bond substantially prevents the chemical compound from transferring to the patient, wherein the chemical compound comprises an aluminum oligomer or an aluminum salt.

2. A wound or surgical dressing as defined in claim 1, wherein the aluminum oligomer comprises aluminum chlorohydrate.

3. A wound or surgical dressing as defined in claim 1, wherein the chemical compound comprises particles coated with a cationic polymer or a cationic oligomer.

4. A wound or surgical dressing as defined in claim 1, wherein the chemical compound is applied to a treated area on the substrate, the chemical compound being applied to the treated area in an amount from about 0.01% to about 20% by weight.

5. A wound or surgical dressing as defined in claim 1, wherein the chemical compound is applied to a treated area on the substrate, the chemical compound being applied to the treated area in an amount from about 0.05% to about 10% by weight.

6. A wound or surgical dressing as defined in claim 1, wherein the chemical compound is crosslinked.

7. A wound or surgical dressing as defined in claim 1, wherein the substrate comprises a gauze.

8. A wound or surgical dressing as defined in claim 1, wherein the substrate comprises an elastic material.

9. A wound or surgical dressing as defined in claim 8, wherein the elastic material comprises a stretch-bonded laminate or a neck-bonded laminate.

10. A wound or surgical dressing as defined in claim 1, wherein the substrate comprises a spunbond web, a meltblown web, or a laminate thereof.

11. A wound or surgical dressing as defined in claim 1, wherein the substrate comprises a spunbond/meltblown/spunbond laminate.

12. A wound or surgical dressing as defined in claim 1, wherein the substrate comprises a coform web.

13. A wound or surgical dressing as defined in claim 1, wherein the substrate comprises an airlaid web.

14. A wound or surgical dressing as defined in claim 1, wherein the substrate comprises a bonded carded web, a wetlaid web, a foam, a film, a woven fabric, or a knitted fabric.

15. A wound or surgical dressing as defined in claim 1, wherein the substrate comprises a hydroentangled web.

16. A wound or surgical dressing as defined in claim 15, wherein the hydroentangled web comprises pulp fibers and synthetic fibers.

17. A wound or surgical dressing as defined in claim 1, wherein the chemical compound binds with negatively charged bacteria, pathogens, fungi, ions, or molecules.

18. A wound or surgical dressing as defined in claim 1 wherein the chemical compound bonded to the substrate reduces bacterial growth by at least about 50%.

19. A wound or surgical dressing as defined in claim 1 wherein the chemical compound bonded to the substrate reduces bacterial growth by at least about 90%.

20. A wound or surgical dressing as defined in claim 1 wherein the chemical compound bonded to the substrate reduces bacterial growth by at least about 99%.

21. A wound or surgical dressing as defined in claim 1, wherein the wound or surgical dressing comprises an adhesive bandage.

22. A wound or surgical dressing as defined in claim 1, wherein the wound or surgical dressing comprises a wrapping.

23. A wound or surgical dressing comprising:
   a substrate comprising cellulosic fibers and configured to contact or surround a wound or surgical site, the substrate comprising a material selected from the group consisting of gauze, a stretch-bonded laminate, a neck-bonded laminate, a spunbond web, a meltblown web, a coform web, an airlaid web, a wetlaid web, and a hydroentangled web; and
   a chemical compound applied to the substrate, the chemical compound being located on the substrate so as to contact a patient at or near a wound or surgical site, the chemical compound being covalently bonded to the cellulosic fiber of the substrate so that the chemical compound does not substantially transfer to the patient, the chemical compound having a net positive charge for binding with negatively charged matter, the chemical compound comprising an aluminum salt, an aluminum ion, an aluminum complex, an aluminum molecule, or an aluminum oligomer.

24. A wound or surgical dressing as defined in claim 23, wherein the chemical compound comprises particles.

25. A wound or surgical dressing as defined in claim 23, wherein the chemical compound comprises aluminum chlorohydrate.

26. A wound or surgical dressing as defined in claim 1, wherein the aluminum oligomer comprises aluminum chlorohydrol.

27. A wound or surgical dressing as defined in claim 1, wherein the chemical compound comprises aluminum particles.

28. A wound or surgical dressing as defined in claim 1, wherein the chemical compound comprises alumina particles.

29. A wound or surgical dressing as defined in claim 23, wherein the aluminum oligomer comprises aluminum chlorohydrol.

* * * * *